United States Patent
Hacker et al.

(10) Patent No.: US 6,860,486 B2
(45) Date of Patent: Mar. 1, 2005

(54) SHAFT SEALING RING

(75) Inventors: Gunther Hacker, Elmenhorst (DE); Rolf Johnen, Wiemersdorf (DE); Wolfgang Schmitt, Viernheim (DE)

(73) Assignee: Dichtungstechnik G. Bruss GmbH & Co. KG, Hamburg (DE)

( * ) Notice: Subject to any disclaimer, the term of this patent is extended or adjusted under 35 U.S.C. 154(b) by 0 days.

(21) Appl. No.: 10/287,589

(22) Filed: Nov. 5, 2002

(65) Prior Publication Data

US 2003/0085527 A1 May 8, 2003

(30) Foreign Application Priority Data

Nov. 8, 2001 (DE) .......................................... 101 54 799

(51) Int. Cl.[7] .............................................. F16J 15/32
(52) U.S. Cl. ...................... 277/553; 277/549; 277/559; 277/560; 277/562
(58) Field of Search .............................. 277/549, 553, 277/559, 560, 562

(56) References Cited

U.S. PATENT DOCUMENTS

| | | | | |
|---|---|---|---|---|
| 5,921,555 A | * | 7/1999 | Johnston | ..................... 277/559 |
| 6,401,322 B1 | * | 6/2002 | Matsushima | .................. 29/460 |
| 6,520,507 B2 | * | 2/2003 | Pataille et al. | .............. 277/561 |
| 2002/0158421 A1 | * | 10/2002 | Johnston | ..................... 277/549 |

* cited by examiner

Primary Examiner—Alison Pickard
Assistant Examiner—Enoch Peavey
(74) Attorney, Agent, or Firm—Duane Morris LLP

(57) ABSTRACT

A shaft sealing ring for a shaft comprises a sealing lip made of an elastomeric material or a PTFE compound and dimensioned as to be flaccidly bendable. The flexural elasticity is selected such that it will just be sufficient to press a sealing portion of the sealing lip into sealing engagement with the periphery of the shaft. The sealing portion of the sealing lip engages the periphery for a predetermined length. In the sealing portion, the sealing lip is provided along its circumference, at the side of the shaft, with endless, undulating return channels at least throughout this length. These channels return any medium escaping during rotation of the shaft to the space to be sealed. The return channels do not communicate with the surroundings of the shaft sealing ring. No seperate contact pressure means, such as a helical ring coil spring is required to press the sealing lip into engagement with the shaft.

15 Claims, 1 Drawing Sheet

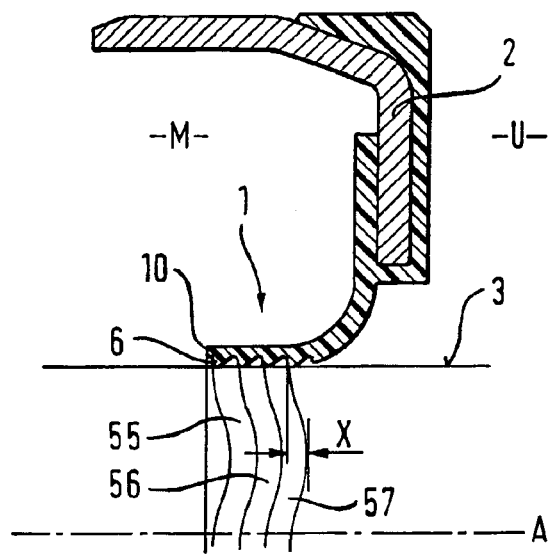
Fig. 1
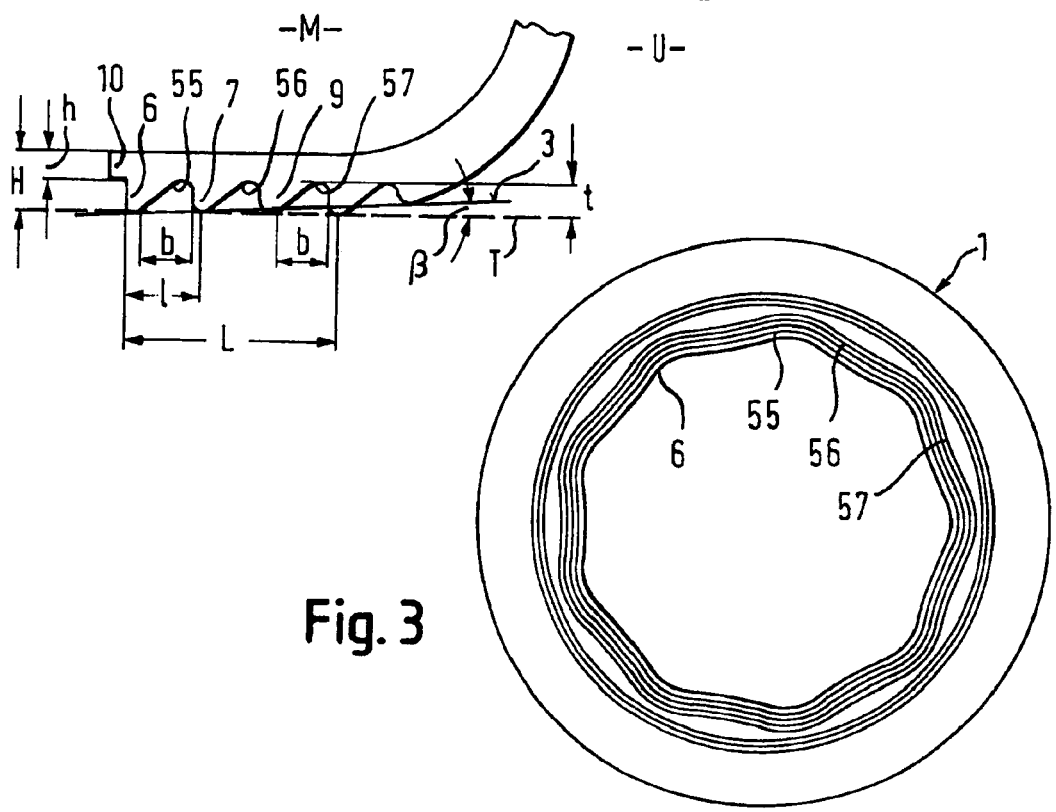
Fig. 2
Fig. 3

SHAFT SEALING RING

The instant invention relates to a shaft sealing ring having a sealing lip which is made of an elastomer.

BACKGROUND

During the past few years shaft sealing rings of elastomeric material often were replaced by shaft sealing rings whose sealing lips were made of polytetrafluoroethylene (PTFE) when intended for sophisticated applications, such as to be used in modem internal combustion engines. It has been suggested with such shaft sealing rings to provide a thread in a sealing portion thereof which will be in engagement with a surface area of the shaft, when the shaft sealing ring is mounted, so as to return the medium to be retained (lubricant) back into the space to be sealed when the shaft rotates (cf. H. K. Mueller "Abdichtung bewegter Maschinenteile", 1990 Medienverlag Ursula Mueller, pages 42, 43, picture 18-RD).

A problem with such shaft sealing rings having a sealing lip of PTFE is that they seal only "dynamically", in other words, when the shaft is rotating and, what is more, just in one direction of rotation. "Statically", in other words with the shaft at standstill, they leak.

In connection with radial shaft sealing rings having an essentially radially oriented elastomer sealing lip, so-called hydrodynamic sealing aids are known which operate in the manner of "windshield wipers" (cf. pages 39, 40 and picture 14-RD of the book cited above by H. K. Mueller). Such shaft sealing rings, as a rule, are provided with a ring coil spring also known as "worm spring" to press the sealing lip against the periphery of the shaft. The radial contact pressure exerted by the worm spring, which pressure represents the contact pressure of the sealing lip in relation to the shaft periphery, normally lies in a range between 0.8 and 1.6 N/cm.

Faulty or forgotten mounting of the spring or its popping off while manipulating the shaft sealing ring before or during assembly of the shaft sealing ring is known to cause early failure. Elastomer sealing lip designs featuring a tip which engages the shaft in almost linear contact and under very high surface area pressure result in very high excess temperature and undesirable chemical reactions of the medium to be retained and/or the elastomer material of the seal and, therefore, cause damage in the contact zone of the sealing lip. That normally reduces the service life.

Also known is a radial shaft sealing ring, preferably made of PTFE which comprises a return flow means embodied by a groove adjacent the sealing edge. More precisely, this return means is composed of sinusoidal undulations oriented in circumferential direction and having a wedge-shaped inner profile, as seen in the direction of the space to be sealed (EP 0 798 498 B 1). This known radial shaft sealing ring is said to be effective regardless of the direction of rotation of the shaft to be sealed.

It is the object of the invention to provide a shaft sealing ring including a sealing lip of elastomeric material which will afford effective, reliable, dynamic sealing even at high circumferential speeds and vibrational loading of the shaft, irrespective of the direction of rotation thereof. It is another object of the invention to prolong the service life of the shaft sealing ring in comparison with known shaft sealing rings having an elastomer sealing lip and, furthermore, to warrant static sealing and to avoid premature failure. Moreover, a shaft sealing ring of the kind defined is to be easy to manufacture, thus allowing inexpensive production.

These objects are met by the shaft sealing ring disclosed herein.

A shaft sealing ring according to the invention has at least one undulating, closed, continuous return channel extending around the circumference of the sealing lip at least for a predetermined axial length throughout which the sealing lip engages the surface of the shaft. The return channel conveys exiting medium back to the space to be sealed while the shaft rotates.

Moreover, it assures that the shaft is wetted by the medium in the area of contact with the sealing lip, in other words it lubricates the shaft.

The flaccidly bendable or flexible design of the elastomer sealing lip allows a sealing portion of the sealing lip, by virtue of its flexural elasticity, to come to lie snugly tangentially against the periphery of the shaft across the predetermined length thereof, when mounted. The flexural elasticity is to be selected such that it will assure dynamic sealing in both directions of rotation of the shaft, without any need for the customary worm spring because the sealing portion will accompany vibrational motions of the shaft for being soft and pliable or flaccid.

The contact pressure is reduced, in comparison with a conventional solution according to which the sealing lip is pressed against the shaft surface at high specific pressure by means of a worm spring which acts merely through a tip. Here, the sealing portion engages the shaft surface in a surface area of predetermined axial length which covers the front edge at the side facing the medium and the rear edge at the side facing the surroundings of the first and other return channels, if any. In this manner friction is reduced so that excess temperatures which would damage the sealing lip cannot be generated any more. That contributes substantially to prolonging the service life.

The edge of the sealing lip facing the medium either may not be undulated, or it may be undulated in parallel with the one or more return channels.

A manufacturing advantage is obtained with both alternatives if the edge of the sealing lip facing the medium is provided, radially outside, with an axial cylindrical annular projection.

In that way the design of the mold for making the sealing lip is greatly simplified.

The "sealing edge" defined by the first return channel, including both its front and rear edges, is fully covered by the length "L" throughout which the sealing lip engages the shaft. Thus the medium which exits from the space to be sealed is reliably returned into that space. It is an essential feature of the invention that the rear edge facing the surroundings is pressed into contact with the periphery of the shaft by at least the same amount of pressure as the front edge of the first return channel which is oriented towards the medium. That is achieved by the selection of an angle of inclination "β" of the tangent to the front edge of the first return channel facing the medium and to the rear edge of this first return channel facing the surroundings or, in the case of a plurality of return channels, the last one upstream of the surroundings end. The sealing lip is to be dimensioned in such a way that this condition will be fulfilled even if the shaft sealing ring is installed eccentrically and/or the shaft rotates eccentrically.

According to the invention, therefore, the design engineer can adjust the contact pressure distribution as desired in the manner specified.

With sealing sleeves made of an elastomeric material having a hardness from approximately 70 to 80 IRHD, the angle β lies in a range between 0° and 5°, preferably between 1 and 3°.

The first return channel preferably is followed by other return channels, axially spaced from the first one in the direction towards the surroundings. In that event the tangent mentioned above touches the front edge of the first return channel facing the medium and the rear edge of the last return channel facing the surroundings.

The courses of the one or more return channels preferably are sinusoidal or composed of interconnected circular arc segments which are alternatingly curved in opposite directions.

A shaft sealing ring according to the invention effectively seals also when the shaft is not moving, in other words it seals statically. When the shaft rotates the shaft sealing ring seals dynamically in both directions of rotation of the shaft.

The fact that an additional contact pressure means, such as a worm spring is dispensed with not only reduces the contact pressure at which the sealing sleeve is pressed against the shaft, it also permits manufacture in one piece, whereby reliability is improved and production costs are lowered. Values applicable in practice for selecting the mean radial contact pressure referred to the periphery of the shaft for elastomer sealing sleeves are about 0.8 N/cm, so far the lowermost value obtainable for conventional radial shaft sealing rings. Preferably, they lie in a range between 0.1 and 0.4 N/cm.

Shaft sealing rings according to the invention are applicable, above all, in cases where sealing must be obtained in both directions of rotation and high excess temperatures must be avoided in the zone of contact between seal and shaft in order to prevent undesirable chemical reactions of the sealing ring with the medium to be retained. Such applications are given in motor vehicles, above all in gear shift mechanisms, gear drives connected downstream of converters, differential gears, and axles.

Advantageous further developments, in particular advantageous dimensioning measures are covered by the dependent claims.

The invention will be described further, by way of example, with reference to the accompanying drawings, in which:

BRIEF DESCRIPTION OF THE DRAWINGS

FIG. 1 is a part cross sectional elevation of a shaft sealing ring including an elastomer sealing lip according to the invention;

FIG. 2 shows a sector of the shaft sealing ring illustrated in FIG. I on an enlarged scale;

FIG. 3 is a front elevational view of a shaft sealing ring according to the invention before its installation.

DETAILED DESCRIPTION

A shaft sealing ring shown in the figures for a shaft whose periphery is designated 3 comprises a sealing sleeve with a sealing lip made of an elastomer and connected directly to a stiffening plate 2 by vulcanizing. By virtue of its dimensioning, the sealing lip is flaccidly bendable, i.e. easily to be bent, and it is not pressed against the periphery 3 of the shaft by a separate spring such as a worm spring as usual.

When not installed, the sealing lip 1 is stretched out radially (cf. FIG. 3) and has an inner diameter which is smaller than the outer diameter of the shaft to be sealed. Once mounted, the sealing lip 1 is curved, as illustrated in FIG. 2, in a direction parallel to the axis of the shaft so that the sealing lip I approaches the shaft tangentially and has a cylindrical portion 11 entering into surface area engagement, along an axial length L, with the periphery of the shaft under slight contact pressure caused alone by the flexural elasticity of the sealing lip 1. The dimensions of the sealing lip are selected such that the contact pressure referred to the periphery 3 of the shaft will be in a range between 0.1 and 0.8 N/cm, preferably between 0.1 and 0.4 N/cm.

Sinusoidally undulated return channels are cut out in the form of endless grooves 55, 56, 57 at the side of the sealing lip 1 facing the surroundings U. At least the first groove 55 extends within the length L of the portion 11 of the sealing sleeve so that any medium which has escaped the space M to be sealed can be returned into said space M by the groove 55 over the front edge 6 of the sealing lip 1, which edge is oriented towards the medium. In the embodiment shown in the figures the front edge 6 is undulated parallel to the groove 55, at the same amplitude and the same period. The length L is chosen such that at least the two grooves 55 and 56 following the edge 6 which faces the medium are completely covered tightly by the shaft surface, in other words the front edge 6 as well as rear edges 7 and 9 which are oriented towards the surroundings are continuously in sealing contact with the periphery 3 of the shaft, whereby at least these grooves 55, 56 do not communicate with the surroundings U so that leakage to the surroundings U is impossible.

In principle, groove 55 has the same curvature as the edge 6 of the sealing lip which faces the medium and engages the periphery 3 of the shaft.

Advantageous dimensioning measures may be gathered from FIG. 3. They relate to the dimensions of the sealing lip 1 and will be explained in greater detail below.

The sector of the sealing lip shown in FIG. 2 in the same position as in FIG. 1 is mounted on the shaft (not shown) and bent at an angle of 90°; it comprises three return channels 55, 56, 57 which are shown in part The following reference letters designate:

L—axial length of the area of contact between the sealing lip and the shaft t—depth of the grooves l—axial spacing between two grooves H—total thickness of the sealing lip 1 h—effective sealing lip thickness in the area of the grooves

A—direction of the shaft axis

T—tangent to edges 6 and 7

β—angle of inclination of tangent with respect to A

X—amplitude of undulation of the grooves.

The grooves 55, 56, and 57 shown in FIG. 2 earch are limited by rear edges 7 and 9 towards the surroundings U. The edge 7 following the first groove 55 projects farther radially inwardly than the front edge 6 facing the medium. That is demonstrated in FIG. 2 by the tangent T to the edge 6 and its angle β of inclination with respect to the axial direction A of the periphery 3 of the shaft. The tangent T is drawn in dashed lines and starts from the tip of the edge 6. In FIG. 2 the edges 7, 9 are shown undeformed. However, it may be recognized from FIG. 2 to what amount the said edges become upset respectively if one looks at the increasing distances between the tangent T and the periphery 3 of the shaft from left to right in FIG. 2.

This is what provides the desired greater contact pressure of these edges against the periphery 3 of the shaft. In practice, when using an elastomer of a Shore-A hardness between 70 and 80, the angle β will be between 1° to 5°, preferably between 1° and 3°.

Due to this dimensioning the rear edges 7, 9 each will be pressed against the periphery 3 of the shaft at an increasingly higher contact pressure than the front edge 6. Thus it is made sure that the groove 55 will be blocked towards the surroundings U.

The grooves 55 and 56 in any case will not communicate with the surroundings U due to the static contact pressure of the sealing lip 1 against the periphery 3 of the shaft in the area of the length L and, therefore, lubricating oil is reliably prevented from escaping into the surroundings U when the shaft is not rotating. Thus "static" sealing is guaranteed.

Studies by the inventors have shown that the following relationships and dimensional ranges should be observed in order to obtain the desirable flexing behavior of the sealing lip 1:

$L/1 \geq 2.0$, preferably: $2.3 < L/1 \leq 3.2$ $0.25 \text{ mm} < h \leq 1 \text{ mm}$, preferably: $0.5 \text{ mm} < h \leq 0.9 \text{ mm}$ $1° < \beta \leq 5°$, preferably: $1° < \beta 3°$ $L/X < 1.0$.

The endless grooves 55, 56, and 57 serve not only to return medium (oil) to the medium side M but also to wet the sealing lip 1 in its area of contact with the shaft. Thus they contribute to obtaining good sealing effect and a longer service life of the shaft sealing ring.

A mold of complicated structure is required for forming the sealing lip with a sealing edge which is undulated in circumferential direction. If, however, the sealing lip is extended in axial direction in its part which is situated above the return channels by forming a cylindrical annular projection 10 (cf FIGS. 1 and 2) then this annular projection can be given an edge at right angles to the circumferential direction. Thus the full shape of the undulated return channels can be incorporated in the core of a conventional three-part mold. In this manner the mold costs can be greatly reduced and handling of the mold during production becomes much simpler.

The edge of the projection 10 facing the medium may be undulated like the return channels 55 to 57, but it may also be rectilinear, i.e. cut off cylindrically.

The features disclosed in the specification above, in the claims and drawings may be essential to the implementation of the invention in its various embodiments, both individually and in any combination.

What is claimed is:

1. A shaft sealing ring comprising the following features:
   (a) the shaft sealing ring includes a sealing lip which is made of an elastomer;
   (b) the sealing lip is flaccidly bendable or flexible, its flexural elasticity being chosen sufficiently great to press a sealing portion of the sealing lip into sealing engagement with the periphery of the shaft, without any additional contact pressure means;
   (c) at the side of the shaft, the sealing lip is provided with at least one undulating, closed, continuous return channel around the circumference of the sealing lip, which channel acts to return exiting medium during rotation of the shaft to the space to be sealed and is blocked towards the surroundings;
   (d) the sealing portion of the sealing lip engages the periphery of the shaft for a predetermined axial length which is dimensioned at least so that the sealing lip will fully contact the periphery of the shaft both at the front edge of the at least one or each return channel at the side facing the medium and at the rear edge of the at least one or each return channel facing the surroundings;
   (e) the rear edge of the first return channel facing the surroundings is pressed into contact with the periphery of the shaft by at least the same amount of pressure as the front edge of the first return channel facing the medium;
   (f) the tangent to the front edge facing the medium and to the rear edge of the first or last return channel facing the surroundings is inclined with respect to the axial direction of the shaft of an angle of inclination in the range between 1° and 5°.

2. The shaft sealing ring as claimed in claim 1, characterized in that the edge of the sealing lip facing the medium is undulated in parallel with the return channel or channels.

3. The shaft sealing ring as claimed in claim 1, characterized in that, radially outside, the edge of the sealing lip facing the medium comprises an axial cylindrical annular projection.

4. The shaft sealing ring as claimed in claim 1, characterized in that at least one other return channel is provided axially next to the first return channel in the direction towards the surroundings.

5. The shaft sealing ring as claimed in claim 4, characterized in that the return channels are undulated alike with the same respective amplitude and period.

6. The shaft sealing ring as claimed in claim 1, characterized in that the course of the return channel or channels is sinusoidal.

7. The shaft sealing ring as claimed in claim 1, characterized in that the return channel or channels is/are made up of interconnected circular arc segments which are alternatingly curved in opposite directions.

8. The shaft sealing ring as claimed in claim 1, characterized in that the or each return channel is embodied by a circumferential endless groove of which the depth to width ratio lies in the range of from 0.3 to 1.0.

9. The shaft sealing ring as claimed in claim 8, characterized in that the effective thickness of the sealing lip in the area of the groove, as measured from the bottom of the groove, lies in the range of from 0.25 to 1 mm.

10. The shaft sealing ring as claimed in claim 9, characterized in that the effective thickness of sealing lip in the area of the groove, as measured from the bottom of the groove, lies in the range of from 0.5 and 0.9 mm.

11. The shaft sealing ring as claimed in claim 1, characterized in that the sealing contact pressure of the sealing lip referred to the periphery of the shaft lies in the range between 0.1 to 0.8 N/cm.

12. The shaft sealing ring as claimed in claim 11, characterized in that the sealing contact pressure of the sealing lip referred to the periphery of the shaft lies in the range between 0.2 to 0.5 N/cm.

13. The shaft sealing ring as claimed in claim 1, characterized in that the axial spacing between the two adjacent return channels is smaller than the amplitude of the sinusoidal undulation of the return channels.

14. The shaft sealing ring as claimed in claim 1, characterized in that the angle of inclination of the tangent is from 1° to 3°.

15. The shaft sealing ring as claimed in claim 1, characterized in that the or each return channel is embodied by a circumferential endless groove of which the depth to width ratio lies in the range of from 0.3 and 0.7.

* * * * *